United States Patent [19]
Babson

[11] 3,947,378
[45] Mar. 30, 1976

[54] ADSORBED PLASMA
[75] Inventor: Arthur L. Babson, Chester, N.J.
[73] Assignee: Warner-Lambert Company, Morris Plains, N.J.
[22] Filed: Dec. 23, 1974
[21] Appl. No.: 535,879

[52] U.S. Cl. ................ 252/408; 23/230 B; 195/99; 195/103.5 R; 424/2
[51] Int. Cl.² ................ G01N 1/00; G01N 33/16; G01N 11/00; G01N 31/06
[58] Field of Search ........ 252/408; 23/230 B; 424/2; 195/103.5 R, 99

[56] References Cited
UNITED STATES PATENTS

| | | | |
|---|---|---|---|
| 3,179,567 | 4/1965 | Owren | 195/103.5 R |
| 3,293,134 | 12/1966 | Lenahan et al. | 252/408 |
| 3,395,210 | 7/1968 | Lenahan et al. | 23/230 B |
| 3,486,981 | 12/1969 | Speck | 252/408 |
| 3,634,581 | 1/1972 | Thomas | 252/408 |
| 3,799,885 | 3/1974 | Dennis et al. | 252/408 |
| 3,853,710 | 12/1974 | Innerfield | 23/230 B |
| 3,880,714 | 4/1975 | Babson | 195/103.5 R |

OTHER PUBLICATIONS

Proctor, R. R. and Rapaport, Samuel I.; Am. J. Clin. Path., Vol. 36, No. 3 pp. 212–219 (Sept. 1961).
Tullis, J. L.; "Blood Cells and Plasma Proteins," Academic Press Inc. New York, pp. 61–74 (1953).

*Primary Examiner*—Benjamin R. Padgett
*Assistant Examiner*—T. S. Gron
*Attorney, Agent, or Firm*—Albert H. Graddis

[57] ABSTRACT

The present invention relates to an improved process for the production of a deficient citrated plasma useful in the clinical laboratory as a control plasma for the testing of clotting function, and particularly, in patients who are on oral anticoagulant thereapy.

1 Claim, No Drawings

ADSORBED PLASMA

The use of oral anticoagulants is an accepted form of therapy in the management of patients suffering from various thrombo-embolytic conditions and this therapeutic approach finds utility on both a short-term and a long-term basis. Since anticoagulants exert their anticoagulant effect by interfering with one or more steps in the coagulation mechanism, thereby preventing additional thrombi, their clinical effect on the patient must be carefully monitored by suitable laboratory tests in order to minimize or avoid haemorrhagic complications while providing therapeutic anticoagulation. These complications may take the form of massive gastro-intestinal bleeding from unsuspected peptic ulcer or intestinal obstruction may result from interstitial bleeding in the wall of the bowel. Subdural haematoma is also a well-documented complication. For these reasons both the initial anticoagulant dosage and the maintenance dosage must be carefully prescribed and the course of the prescribed anticoagulant therapy both on the short-term and the long-term basis must be carefully monitored by clinical laboratory tests of the clotting function in order to maintain the anticoagulant effect of the therapy employed within the desired range.

The orally administered anticoagulants produce their anticoagulant effect by inhibiting prothrombin (Factor II) and diminishing its concentration in addition to several of the blood factors needed in prothrombin conversion, Factors VII and X in the extrinsic blood coagulation system and Factors IX and X in the intrinsic blook coagulation system. Thus, the anticoagulant effect of oral therapy may be measured by testing a patient's plasma for the effect on coagulation which is produced by the decrease in the concentration of these factors produced by the anticoagulant. The extent to which the time of coagulation of a blood sample has been increased can be demonstrated by the one-stage prothrombin time. While the apparent increase in coagulation time over what is the generally accepted normal range of blood coagulation times can thus be determined, the many variables involved including the subjective response of the technician running the test or the particular instrument on which it is run make it essential that the test be effectively monitored and that coagulation control plasmas be run along side of the coagulation test of the patient's plasma. In this way variations in subjective reactions may be minimized and differences between instruments cancelled out.

To effectively monitor coagulation tests on abnormal patient plasma, standardized control plasmas are necessary in which the level of those factors whose absence is responsible for the coagulation defects is such as to put the control plasma in the abnormal range also. Thus, by comparing the one-stage prothrombin time of an unknown plasma to the one-stage prothrombin time of the abnormal control plasma in which the reduced level of clotting factors is known and carrying out the determinations at the same time it is relatively easy to determine the status of the patient. Since the level of Factors II, VII, IX and X is affected by oral anticoagulants the use of control plasmas having decreased levels of these factors but normal levels of the other factors will give an indication of the effect on a patient of oral anticoagulant therapy and determine whether or not the dose level should be increased, decreased or maintained at current level.

To produce a control plasma deficient in Factors II, VII, IX and X, citrated plasma is usually treated with $Al(OH)_3$ and if suitable proportions are used these factors are substantially all adsorbed. The use of $Al(OH)_3$ for adsorbing these factors does have one disadvantage in that it is exceedingly difficult to remove all of the residual $Al(OH)_3$ utilized for the adsorption step and traces of this adsorbent remain behind as a contaminant.

While barium sulfate will also adsorb these factors from blood plasma it had been recommended that when this adsorbent was to be used it was to be used only with oxalated blood plasma since it would not adsorb in the presence of citrate. For its use in oxalated plasma the recommendation made was that 1 gram of barium sulfate was to be used for each 10 ml of fresh oxalated plasma when carrying out the adsorption step. However, a real disadvantage with this procedure is that the Factor V present, which is desired to be retained in the control plasma is very unstable in oxalated plasma although quite stable in citrated plasma.

It has now been found, however, that if citrated plasma is treated with about 20 to 22% by weight of barium sulfate a very satisfactory control plasma deficient in Factors II, VII, IX and X is obtained and that the resulting control plasma is very useful as a control standard in the testing of patient plasma where careful monitoring of the patient on oral anticoagulant therapy is necessary. The control plasma obtained retains a satisfactory Factor V level and does not require augmenting the level of this factor in the final product. Furthermore, removal of the barium sulfate adsorbent can be effected completely and yields a more dependable, uniform and reliable control plasma.

In order further to illustrate this invention the following Example is given:

EXAMPLE 1

To 200 ml of fresh pooled citrated blood plasma is added 10 ml of 1 molar HEPES buffer (N-2-hydroxyethyl piperazine N'-2-ethane sulfonic acid) to maintain the pH at 7.35. 150 ml of this buffered plasma is stirred with 33 g of barium sulfate for 30 minutes at room temperature and the barium sulfate separated by centrifugation.

Mixtures of this adsorbed citrated plasma and whole unadsorbed plasma are made and tested for prothrombin time. The concentration of whole plasma required to give prothrombin times of 1½ and 2½ times the normal prothrombin time is determined. The resulting mixtures are then prepared, vials are filled with appropriate volumes and the vial contents lyophilized. The lyophilized material may then be reconstituted with distilled water for production of control plasma.

It has also been noted that in the adsorbed citrated plasma produced by the present process the adsorbed Factors II, VII, IX and X are more uniformly adsorbed so as to reduce the concentration of these factors to about the same level. An unexpected advantage found with the lyophilized abnormal control plasmas produced by mixing the present adsorbed plasma with normal plasma is that they are more stable after reconstitution and give much more uniform results in the activated partial thromboplastin time (APTT) procedure even after storage of up to eight hours or more.

For example, APTT's of sample control plasmas made by $Al(OH)_3$ and $BaSO_4$ adsorption run immediately after reconstitution and eight hours later are shown below:

| Adsorption Process | APTT in Seconds | |
| --- | --- | --- |
| | Initial | 8 Hours Later |
| $Al(OH)_3$ | 62.5 | 46.1 |
| $BaSO_4$ | 60.8 | 60.0 |
| $Al(OH)_3$ | 103.9 | 76.8 |
| $BaSO_4$ | 90.3 | 89.0 |

I claim:
1. In a process for the production of an adsorbed citrated plasma deficient in Factors II, VII, IX and X, the step which comprises stirring citrated plasma with from 20 to 22% by weight of barium sulfate at ambient temperature and then removing the adsorbent from the adsorbed plasma.

* * * * *